United States Patent [19]

Yang

[11] Patent Number: 5,053,029

[45] Date of Patent: Oct. 1, 1991

[54] ABSORBENT PEAT MOSS BOARD PRODUCT

[75] Inventor: Ching-Yun M. Yang, Princeton Junction, N.J.

[73] Assignee: Chicopee, New Brunswick, N.J.

[21] Appl. No.: 464,493

[22] Filed: Jan. 12, 1990

[51] Int. Cl.⁵ .................. A61F 13/15; A61F 13/20
[52] U.S. Cl. .................. 604/385.1; 604/367; 604/374
[58] Field of Search ............ 604/367, 374, 385.1

[56] References Cited

U.S. PATENT DOCUMENTS

| | | | |
|---|---|---|---|
| 2,073,410 | 3/1937 | Thomas | 604/374 |
| 3,343,543 | 9/1967 | Glassman | 604/385.1 |
| 4,215,692 | 8/1980 | Levesque | 604/374 |
| 4,226,237 | 10/1980 | Levesque | 604/375 |
| 4,507,172 | 3/1985 | Levesque | 604/374 |
| 4,605,402 | 8/1986 | Iskra | 604/368 |
| 4,685,914 | 8/1987 | Holtman | 604/367 |

*Primary Examiner*—Randall L. Green
*Assistant Examiner*—Paul Prebilic

[57] ABSTRACT

A disposable absorbent product, such as a urinary pad, comprises a liquid-impermeable, substantially flexible shell, an absorbent core and a liquid permeable facing adhered to the shell so as to enclose the absorbent core therein. The absorbent core comprises at least one layer of tenderized peat moss, each such layer being cut adjacent to each lengthwise edge in one or more slits so as to aid lateral compression folding of the sheet, and, adjacent to the layer of peat moss, a receiving layer of an absorbent cellulosic material. The absorbent core has an M-fold configuration and comprises a longitudinally extending channel for receiving discharged liquid.

19 Claims, 4 Drawing Sheets

ABSORBENT PEAT MOSS BOARD PRODUCT

BACKGROUND OF THE INVENTION

The present invention relates to a new and improved disposable absorbent products such as a urinary pad having high liquid impact capacity, high liquid retention, and which allows the skin of the wearer to remain dry.

Disposable absorbent products have been known for some time, including such products as disposable diapers, sanitary napkins, wound dressings, bandages, incontinent pads, and the like. These products incorporate an absorbent batt which is used to absorb and hold or contain body fluids. Initially in many of these products, especially diapers and sanitary napkins, the absorbent batt comprised what is termed "wadding" or plies of tissue. The wadding was disposed between a liquid-impermeable backing and a liquid-permeable facing and the plies of tissue were used to absorb and, hopefully, contain the liquid within the product. A diaper which utilizes such an absorbent batt is disclosed in U.S. Pat. No. Re. 26,151.

The wadding type of product was replaced, for the most part, by an improved absorbent batt which comprises what is termed "fluffed wood pulp fibers". This absorbent batt comprises a layer of individualized wood pulp fibers with the layer having substantial thickness. A diaper which incorporates such fluffed wood pulp absorbent batt is described in U.S. Pat. No. 2,788,003. This diaper had improved absorbent capacity and somewhat better containment than a diaper using a wadding layer. Also, the fluffed wood pulp layer is quite soft, flexible, and conformable, and, hence, produces an improved diaper over diapers using wadding as the absorbent layer.

Although fluffed wood pulp absorbent batts have a good absorptive capacity, the efficiency with which the capacity is used in a diaper or sanitary napkin is poor. The reason for this is that the fluid to be absorbed is generally deposited in a localized area within the absorbent batt, and the ability of the fluid to move along the plane of the batt is poor. The fluid tends to follow a radial wicking path and consequently moves to the closest edge of the batt where it generally is no longer contained and the product leaks.

In designing a disposable urinary device, one must be mindful of the special problems of an incontinent adult. First, the void of an adult generally is much higher in volume than that of an infant, so a device with greater absorptive capacity than that of an infant's diaper is needed. Second, a bulge under clothing is accepted by society for an infant, but the ambulatory adult with an incontinence problem longs for a product which is not visible through ordinary clothing. Third, the proportions and shape of the legs and torso of the adult differ considerably from those of an infant. Therefore, a mere enlargement of an infant diaper is not a satisfactory product.

A number of years ago, "superabsorbent materials", i.e., materials which will absorb many times their weight of liquid, were developed. Since the development of such materials, attempts to incorporate them in absorbent products such as diapers to enhance the absorption performance of these products have been made. Theoretically, a minimum amount of superabsorbent incorporated in a product would make that product perform as well or better than the prior art products. Perhaps one of the first products to incorporate such a superabsorbent material in a disposable diaper is disclosed in U.S. Pat. No. 3,670,731. This patent discloses an absorbent dressing comprising an absorbent layer sandwiched between a permeable facing and an impermeable backing sheet. The absorbent layer contains water-insoluble cross-linked hydrocolloid polymer as the superabsorbent material.

For numerous reasons, absorbent products employing superabsorbent materials as mentioned above have not to date met with great commercial success. Although the presence of the superabsorbent materials should greatly increase the absorbency of the product, difficulties in processing the materials and in designing a product in which the superabsorbent is evenly dispersed have proven difficult. There thus remains a need for highly absorbent materials which do not pose these problems.

The use of peat moss, in combination with other fibrous materials, for use in absorbent products has previously been suggested. U.S. Pat. No. 4,170,515 to J-M Lalancette discloses a method for bleaching peat moss, thereby making it suitable for use in absorbent dressings and the like. U.S. Pat. No. 4,226,237 to Y. Levesque discloses a layered absorbent structure including a first layer comprising cellulose fibers and, adjacent to the first layer, a second layer comprising, in admixture, peat moss and finely ground mechanical wood pulp. U.S. Pat. Nos. 4,215,692 and 4,507,122, both issued to Levesque, disclose that peat moss, in combination with mechanical wood pulp, can be formed into a low density board, dried, and then compressed to form a thin, flexible, absorbent board which may be used directly in absorbent products. U.S. Pat. No. 4,473,440 to Ovans discloses a peat moss containing board which is manufactured by first conditioning the board to a specific water content and then densifying the board by calendaring between rollers. U.S. Pat. No. 4,676,871 discloses an air laid peat moss board suitable for use in absorbent products which is made by harvesting and individualizing peat moss, drying the peat moss, entraining the peat moss in a gas stream, and then condensing the entrained peat moss to form a low density board. The disclosures of each of these patents are herein incorporated by reference.

Numerous designs for disposable urinary devices have been suggested, none of which, however, utilize a peat moss absorbent element. U.S. Pat. No. 4,685,914 discloses a disposable urinary pad which utilizes superabsorbent material. The pad disclosed in this patent comprises a liquid-impermeable, substantially flexible shell containing a superstructure consisting essentially of a fibrous web of hydrophobic, wet resilient, dry resilient fibers and an absorbent medium in intimate contact with at least a portion of said superstructure and at least a portion of said shell. In a preferred embodiment, the superstructure is a corrugated fibrous web, e.g., of polyester fibers, and the absorbent medium is a superabsorbent material.

U.S. Pat. No. 4,501,586 discloses an absorbent structure comprising a moisture-impermeable backing, an absorbent batt and a moisture-permeable cover covering at least the side opposite the moisture-impermeable backing. The absorbent batt is of loosely-compacted, cellulosic fibers and is provided with a reservoir having a capacity of at least 10 cc. The reservoir is formed by compression of the fibers in the reservoir zone and is located so that the product, when worn, retains the proper shape.

U.S. Pat. No. 4,731,070 discloses an absorbent article particularly suitable for use by male and female incontinents. The absorbent article includes a urine receptacle pocket offset to one end of the product and formed by folding the product and adhering together portions of a moisture impervious sheet that are folded over side marginal edges of an absorbent batt.

The present invention provides a new and improved absorbent product which possesses a large storage capacity, which is soft and comfortable, which can be designed so as not to be apparent through normal clothing and which utilizes the substantial absorptive capacity of peat moss materials.

SUMMARY OF THE INVENTION

The present invention relates to a disposable absorbent product, such as a urinary pad, which comprises a liquid-impermeable, substantially flexible shell, an absorbent core and a liquid-permeable facing adhered to said liquid-impermeable shell, so as to entrap the absorbent core therebetween.

The liquid-impermeable shell is formed from a moldable substance. For example, the shell may be a polyethylene foam shell which is formed from a blown polyethylene foam sheet, subsequently subjected to molding by a thermal process.

The absorbent core includes at least one sheet of tenderized peat moss product. The sheet is generally cut in a rectangular or "racetrack" shape and, to aid lateral compression folding of the sheet, it has been cut to form one or more slits adjacent to each lengthwise edge. The absorbent core also includes, adjacent to the sheet of tenderized peat moss product and disposed upwardly so as to face the wearer of the absorbent product, a receiving layer of an absorbent material. The receiving layer is generally formed of a material which is capable of absorbing body fluid more rapidly than would the peat moss product, but which does not exhibit the overall absorptive capacity of the peat moss product. The receiving layer therefore operates to "receive" and hold the body fluid until it is absorbed by the peat moss product adjacent to it. Preferably, the receiving layer should be capable of absorbing about 120 cc, the volume of a typical adult void. The receiving layer preferably comprises a fibrous web of both wood pulp fibers and non-cellulosic synthetic fibers, e.g., about 50 to 95 weight percent wood pulp and about 5 to 50 weight percent non-cellulosic synthetic fibers.

The absorbent core is pleated in an M-configuration to form therein a center channel in a lengthwise direction. As a result of the pleating, the receiving layer extends down the sides of the pleated core so as to provide a liquid path to the bottom of the core. The pleated absorbent core is placed inside the liquid-impermeable shell and a facing comprising a liquid-permeable web is adhered to the so as to entrap the absorbent core in the shell.

The product of this invention has a high impact capacity, i.e. the product accepts a relatively large quantity of liquid quickly and retains it. Furthermore, the product does not leak or spill over. In other words, once the urine enters the pad, the urine remains entrapped within the product. The product also has a high liquid-holding capacity. In addition, the product maintains its surface dry thereby keeping any moisture away from the skin of the wearer. Still further, the product of this invention permits air circulation in the region where the product is worn which results in a high degree of comfort.

DETAILED DESCRIPTION OF THE INVENTION

Figure 1:
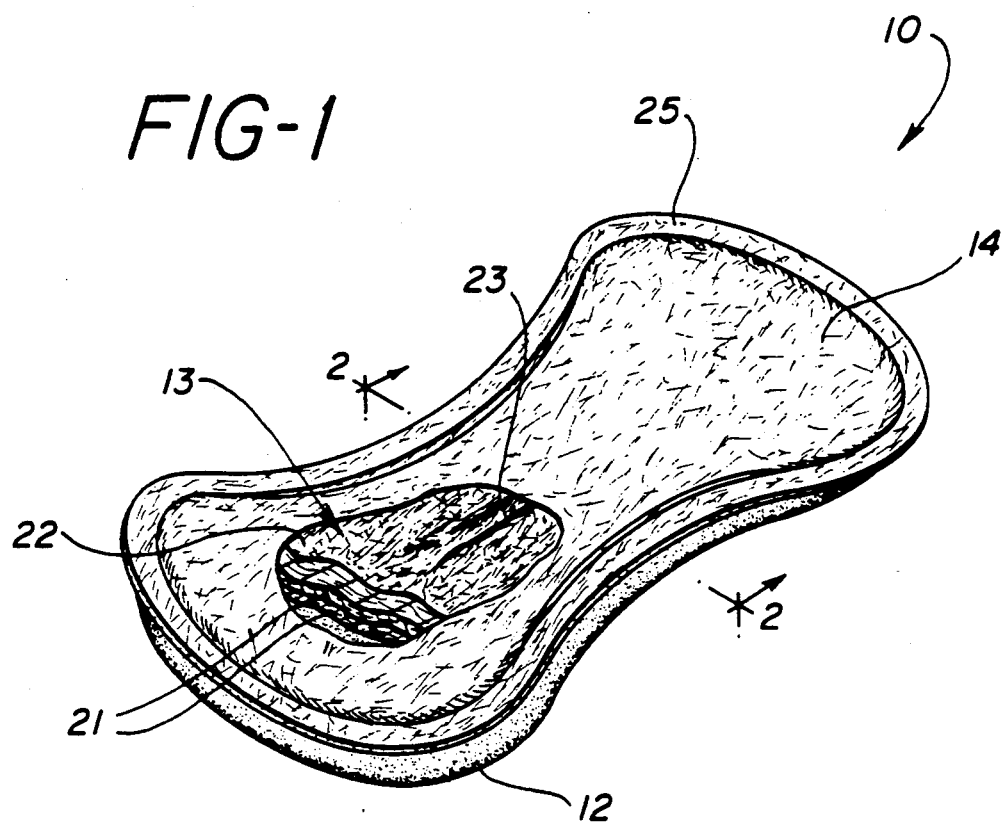
FIG. 1 is a perspective view of a disposable pad of this invention.

FIG. 1 illustrates an embodiment of this invention, a urinary pad 10 in accordance with the teachings of the present invention. The liquid-impermeable backing 12 is a shell which is preformed by a thermal molding process known in the art. Absorbent core 13, pleated in an M-configuration, is fit into the shell 12. The facing 14 is a liquid-permeable, generally hydrophobic fibrous web which may have a typical weight basis of 0.5 oz/yd$^2$. The three elements, the shell 12, the absorbent core 13, and the facing 14, are combined as shown in the drawings, the facing being sealed at its edge to the flange 25 of shell 12 so as to provide a unitary product.

Figure 2:
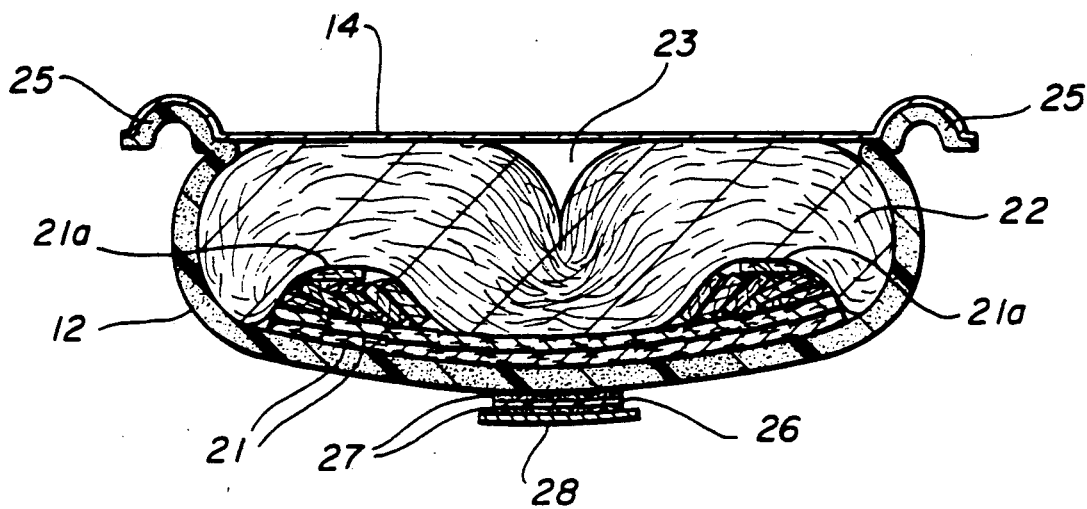
FIG. 2 is a cross-sectional view taken along line 2—2 of FIG. 1.

FIG. 2 is a cross-sectional view of the pad illustrated in FIG. 1. As shown, an absorbent member 21 comprises two layers of a tenderized peat product, and, adjacent thereto, facing upwards towards the wearer of the product, is the receiving layer 22. The absorbent core, comprising at least one layer of peat moss product 21 and the receiving layer 22, is pleated into an M-configuration. In so doing, a channel 23 is created in approximately the center of the pad in a lengthwise direction which can serve to hold discharge until absorbed by the absorbent unit. The M-configured pleats are also advantageous in that they provide lateral compression recovery. Foam shell 12 has upper outwardly extending flanges 25 to which are adhered a liquid permeable facing 14. There are adhesive means 27 on the bottom of the foam shell to facilitate adhering the pad to the wearer's undergarment. Adhesive 27 is protected prior to use by a releasable cover sheet 28.

Figure 3:
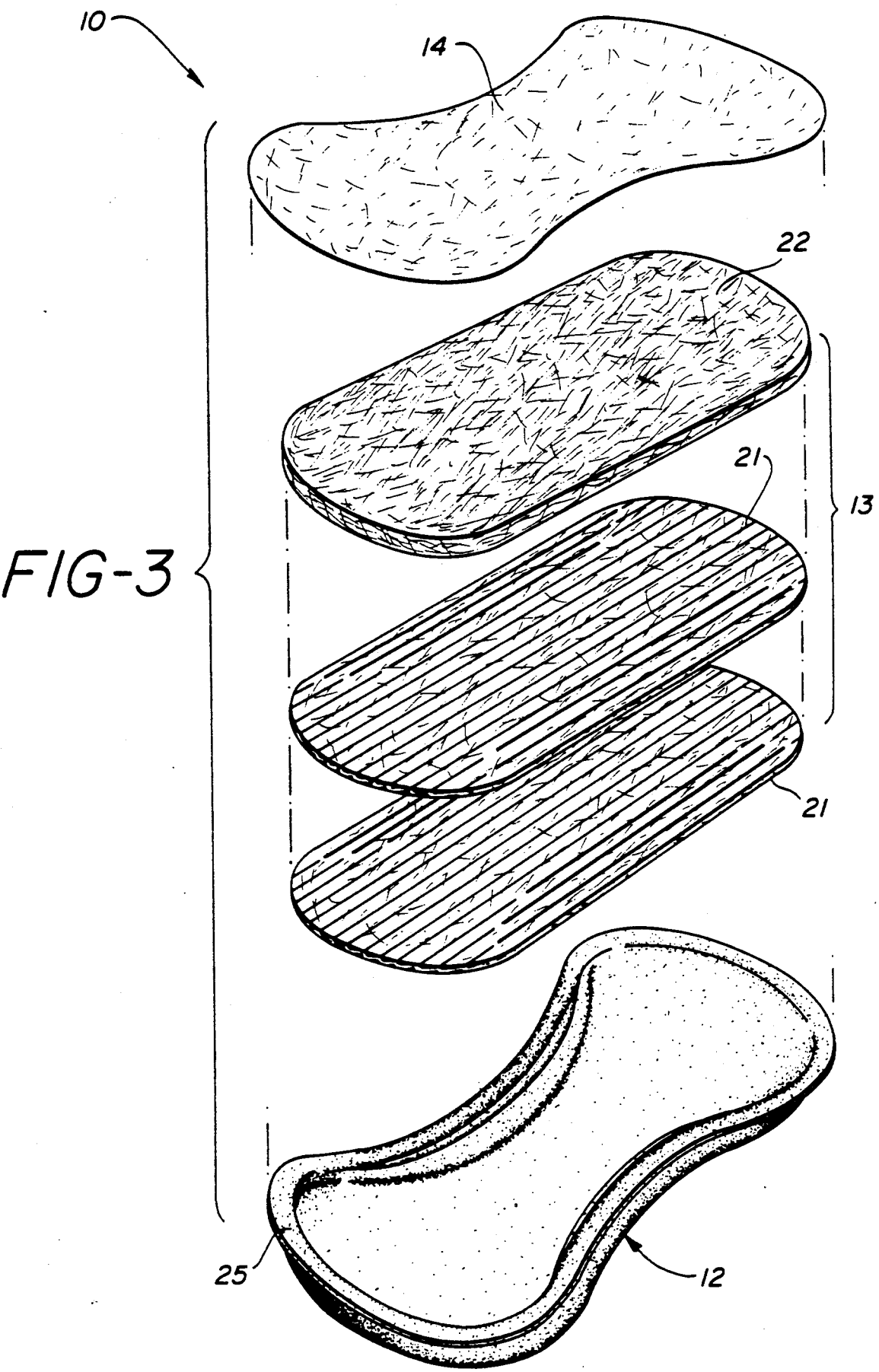
FIG. 3 is an exploded perspective of the structural components of the disposable pad of FIG. 1.

FIG. 3 illustrates the embodiment of a urinary pad of this invention with the elements thereof separated and showing their relationship. Absorbent core 13 comprises at least one layer of peat moss product 21 and the receiving layer 22. This absorbent core, after pleating into the aforementioned M-configuration, is placed inside foam shell 12, and facing 14 is adhered to the flange 25 of the shell to enclose the absorbent core in the shell.

Figure 4:
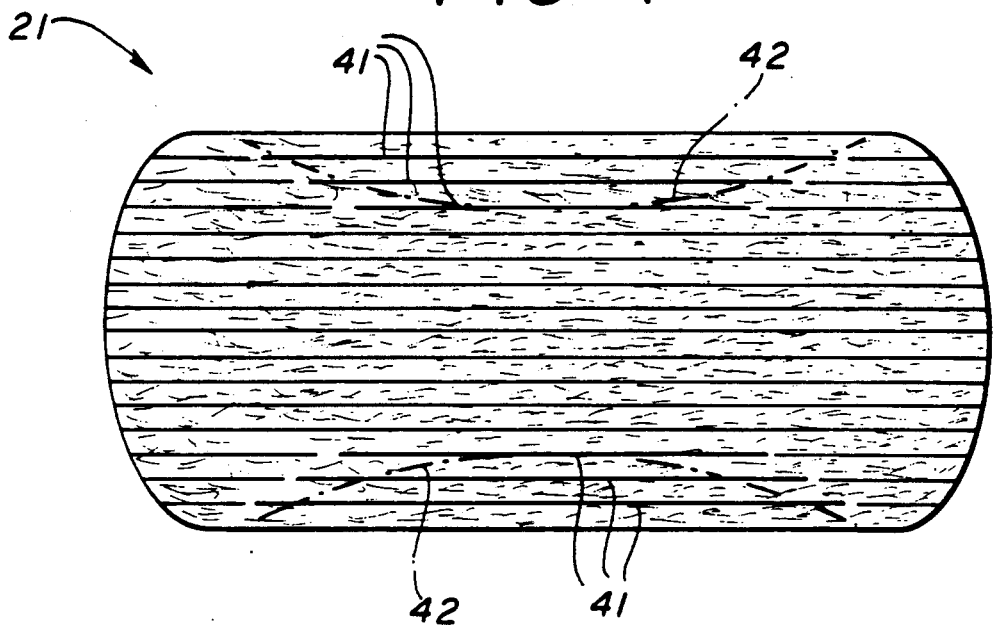
FIG. 4 is a top plan view of a peat moss product useful in the practice of the present invention.

FIG. 4 is a top view of a layer of peat moss product 21 of the illustrated embodiment showing a series of lengthwise slits 41 to allow lateral compression of absorbent core 13. When peat moss product 21 is combined with receiving layer 22 to form absorbent core 13, it is pleated into an M-configuration prior to being inserted into liquid impermeable shell 12. As a result, peat moss product 21 is substantially configured in an hourglass shape as shown by dotted lines 42.

Figure 7:
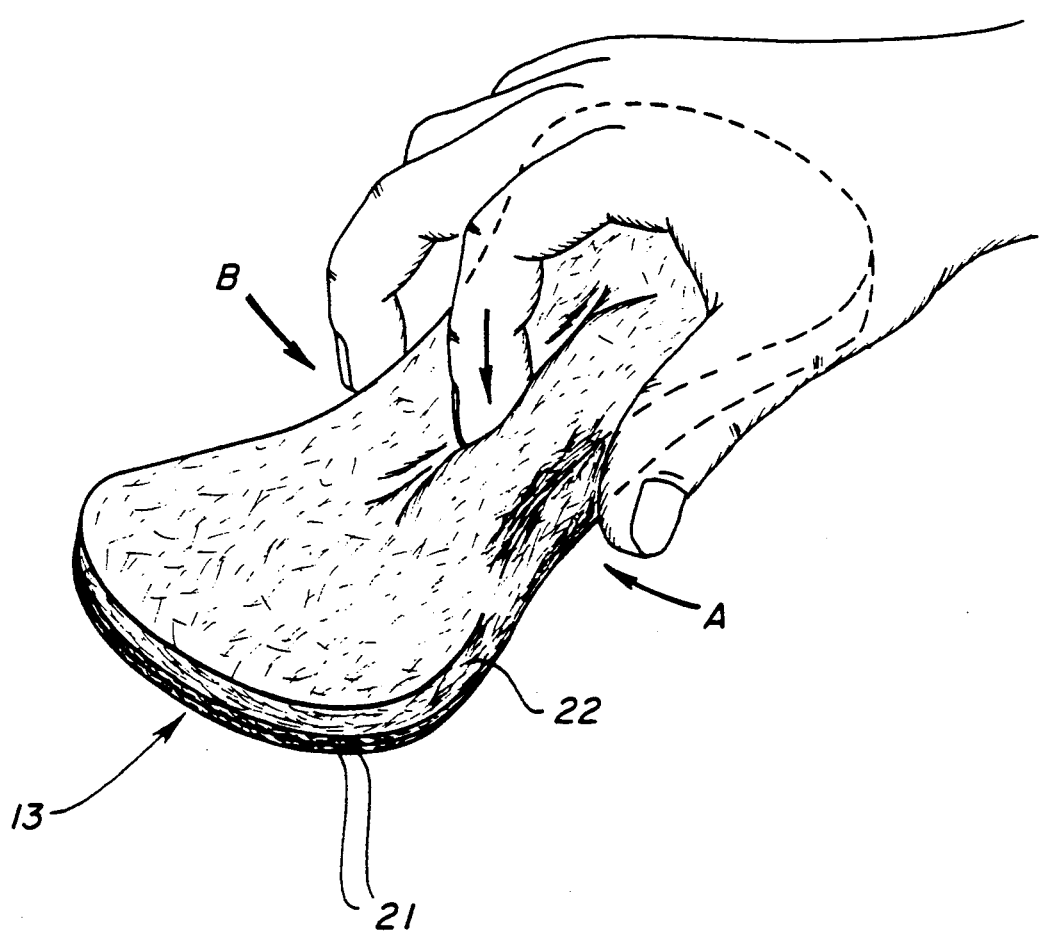
FIG. 7 illustrates a method of providing the absorbent core of FIG. 5 with the folded configuration shown in FIG. 2.

FIG. 7 illustrates a method for forming the M-configured pleat in absorbent core 13. Using a three-finger device (represented by a person's hand in FIG. 7), the center finger remains static while the two outside fingers move toward the center stationary finger, thus causing the M fold and a reduction of the pad width in its center portion. Generally, core 13 is squeezed, as shown, at its center and then placed into liquid impermeable foam shell 12 which holds it in the pleated configuration. The pleats do not have to be restricted to the center portion of the core and could be extended throughout the entire product length.

Since the peat moss product comprising the absorbent core lacks even after appropriate tenderizing, sufficient cross-directional flexibility, lengthwise cuts or slits 41 are made in the product to render it sufficiently flexible to enable it to achieve the required M-fold configuration.

Figure 5:
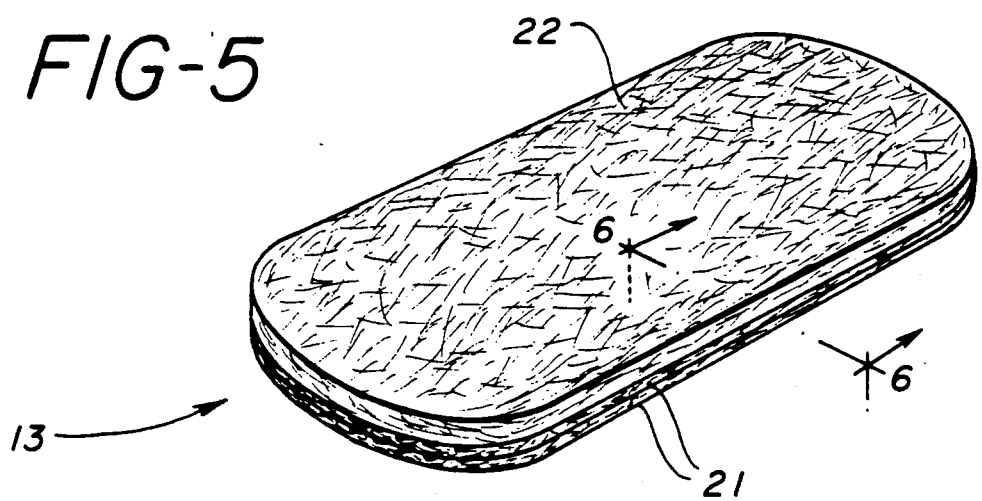
FIG. 5 is a perspective view of an absorbent core comprising the disposable pad of this invention.
Figure 6:
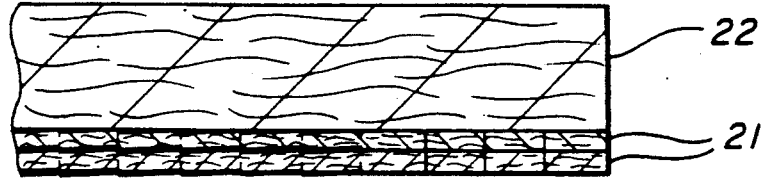
FIG. 6 is a cross-sectional view taken along line 6—6 of FIG. 5.

FIG. 5 is a perspective view, and FIG. 6 is a cross-sectional view, of absorbent core 13 prior to pleating which shows the relationship of the receiving layer 22 and absorbent peat moss layers 21, 21. It will be seen that the three layers are co-extensive and the receiving layer 11 placed on top of the two peat moss layers.

Turning now to a more detailed description of the components of the pad of this invention, the sheet of tenderized peat moss 21 utilized as the absorbent member may be made by methods well known in the art, such as those disclosed in the patents the disclosures of which were previously incorporated by reference. Generally, the raw peat moss material utilized is peat moss of the sphagnum variety and is preferably capable of absorbing at least about 15 times, preferably about 20 times, its weight in water. The peat moss is generally screened and then separated into a usable fraction and peat fines. The screened peat moss may be combined with other absorbent materials, preferably fibrous and cellulosic in nature. These art-recognized materials may include kraft, wood pulp and mechanical wood pulp. As used herein, the term "mechanical wood pulp" is meant to include ground wood pulp, thermomechanical pulp and refiner wood pulp. The common characteristic of these mechanical pulps is that no attempt has been made to separate the fibers by chemical means although they may later, after being reduced to fine particulate matter, be subjected to chemical treatment. Preferably, when mechanical wood pulp is used in the board of this invention, such mechanical wood pulp has a Canadian Standard Freeness (TAPPI TEST METHOD T-227) of from about 60–500 and preferably from about 150–300. Another valuable material used in combination with peat moss is kraft wood pulp. This material is generally a chemically treated, long fibered pulp such as sulfite and sulfate wood pulps. A suitable mixture of ingredients for the absorbent boards of the invention may comprise from about 5 to about 20 percent by weight of kraft wood pulp, with the remainder being essentially peat moss. It is understood that these compositions are preferred peat moss embodiments and that those familiar with the art may find a wide range of peat moss compositions as well as other absorbent materials, i.e., superabsorbents, for use with the products of this invention.

The above peat mixtures can be additionally combined with fibrous means comprising polymer fibers, preferably polyester fibers, and most preferably staple-length polyester fibers. The preferred polyester fibers are disposed to maintain the integrity of the product during processing and use, without subtracting from the intended mechanical flexibility. Preferably the polyester material or other suitable fibrous material is slurried with water in a pulper prior to being mixed with the preferred peat moss compositions. The preferred absorbent elements of this invention can comprise about 2.5% to about 20.0% polyester by weight, preferably about 4.0 to 8.0% polyester by weight. The term "peat moss", then, as used herein to describe the first absorbent member of the absorbent core, is intended to include peat moss products comprising, in addition to particles of peat moss, cellulosic fibers and polymer fibers as described above.

The mixture of screened peat moss and selected fibers are processed into an absorbent element by methods known in the art. Generally, the screened peat moss and selected fibers are slurried together to form an aqueous slurry which is preferably flowed onto a Fourdrinier wire and dewatered to form the starting board. In the most preferred embodiment, a laminate is then made from the peat board and layers of kraft wood pulp. The resulting composite board is then conditioned to a desired moisture content and calendared. This calendaring step serves to densify the composite board and thereby provide it with its necessary high liquid retention capabilities.

The absorbent elements prepared as described above tend not to be flexible enough for use in an absorbent device without undergoing "tenderizing", i.e., processing by any number of known methods to increase the flexibility of the board. See, for example, the disclosure of U.S. Ser. No. 242,274, filed Sept. 12, 1988, which discloses a method of tenderizing the absorbent element by a special cutting process which severs the peat moss portions of the element but which leaves those portions linked with fibrous means to produce a hinge-like effect in the resulting element. The teachings of said U.S. Ser. No. 242,274 are incorporated herein by reference. Other "tenderizing" methods which might be employed to enhance the flexibility of the absorbent board are microcorrugation and perfembossing as disclosed in U.S. Pat. No. 4,605,402 to Iskra.

The absorbent peat moss board is generally cut into a rectangular or "racetrack" shape and, to enhance its cross-directional flexibility, is provided with a plurality of lengthwise slits 41 adjacent each of its lengthwise edges. These slits are preferably several in number along each edge and increase in length from the center of the sheet to the respective side edges. By increasing the cross-directional flexibility of the peat moss board, it is not only easier to shape it in the desired hourglass configuration and fit it into the liquid-impermeable shell, but more of the highly absorbent peat moss material is concentrated in the crotch region of pad 10.

As illustrated in the Figures, one or more layers of peat moss material may be used as the absorbent element. Obviously, the greater the absorptive capacity which is desired for the final product, the more absorptive capacity must be provided in the absorbent core. As the peat moss boards decrease in flexibility with thickness, it may be desired, as illustrated, to utilize two (or more) layers of peat moss board in lieu of one thicker layer.

The material from which the receiving layer is made generally contains wood pulp fibers. Wood pulp is highly wettable, but collapses when wet. Non-cellulosic synthetic fibers such as but not limited to polyolefin fibers (polyethylene, polypropylene, and bicomponent fibers) are just the opposite. They do not collapse as much due to their hydrophobicity. Thus, it has been found that by blending these two materials together, a medium with an optimum absorbency can be obtained. Blending about 5 to 50 weight %, preferably about 20-30 weight %, of non-cellulosic synthetic fibers with the wood pulp fibers leads to a material with markedly improved wet collapse properties compared to straight wood pulp, but which substantially retains the wettability properties of the wood pulp. In the preferred embodiment of this invention, the absorbent medium comprises approximately 80% by weight wood pulp and approximately 20% bicomponent fiber (polyester core/polyethylene sheath fiber of 3d and 1½ staple) and weighs 11 oz/yd². Receiving layer 22 should be capable of absorbing at least about 10 cc of aqueous based liquid (i.e. water or urine) at a rate of 10 cc/second. Preferably, receiving layer 22 is capable of absorbing at least about 50 cc of aqueous based liquid (i.e. water or urine), and more preferably at least 80 cc of said liquid, at a rate of about 10 cc/second.

The absorbent web of wood pulp/noncellulosic synthetic fiber can be prepared by methods known in the art utilizing a transverse webber as disclosed in U.S. Pat. application Ser. No. 99,875, filed Sept. 22, 1987, the disclosure of which is incorporated herein by reference. A roll of pulp board and fiber web may be fed individually to the webber, ground so as to individualize the fibers and then fed into an air stream. The combined pulp/synthetic fiber is collected and thermally bonded together to produce a stable web.

Liquid-impermeable shell 12 is substantially flexible and is generally a polyethylene-containing foam shell which is preformed by a thermal molding process known in the art. The shell generally has a boat-like shape and ranges in thickness from about 1/64 to ¼ inch, preferably about 1/16 inch, in thickness. The shell generally has a length which ranges from about 4 inches to about 12 inches, a width measured from one rim to another across the top space from about 2 inches to about 7 inches, and a depth, measured from a line extending across the width at the upper shell rim in the central portion to the bottom of the shell interior, from about 0.5 to about 2.5 inches. The shell is resilient, when deformed, should substantially return to its original shape.

On the underside of shell 12 there may be placed adhesive attachment means for temporarily, but securely, adhering the shell to the crotch portion of the wearer's nether garment. The attachment means may comprise adhesive lines covered with release strips which, when peeled from the adhesive strips, leave the adhesive ready for use. Preferably, the attachment means comprise a tape 26 coated on both faces with pressure-sensitive adhesive 27, the first face of the tape being permanently adhered to shell 12 and the second face being adapted to be temporarily attached to the wearer's undergarment.

The ethylene-containing polymer foam shell is prepared by known thermal molding processing. One preferred formulation for forming the ethylene-containing polymer foam material is identified as Volara Type A, which is a crosslinked polyethylene foam. The product is manufactured and sold by Voltek, Ind., Lawrence, Mass. The expression "ethylene-containing polymer foam" used herein includes polyethylene homopolymer and ethylene-containing copolymers, preferably containing a major portion, by weight, of ethylene. It is preferred that the polymer present be crosslinked. Preferred comonomers, for preparing the polymers, include vinyl acetate, acrylic and methacrylic acids and esters, such as ethyl acrylate. Blends of such polymers can also be used. Preferably, the formulation is prepared in sheet form at approximately ⅛ inch thickness. The sheet is subjected to thermal molding at a temperature of about 260° F. to form the foam shell.

The liquid-permeable facing 14 provided on the absorbent pad 10 of the present invention may be an apertured film, a nonwoven fabric or a similar material having a high degree of moisture permeability. For example, the nonwoven fabric may be polyester, polyethylene, polypropylene, bicomponent, nylon, rayon, or the like fibers. Preferably, the nonwoven fabric used for facing sheet 14 has a basis weight in the range of 0.3 to 5.0 oz. per square yard and has a density less than 0.2 gms/cc.

The most suitable nonwoven fabrics have high loft, softness and drape characteristics. Though the cover is moisture permeable, it is preferably of the type which after permeation of the moisture, prevents strike-back of the body fluid when the absorbent core is approaching saturation. The facing is readily sealable to the outer rim of the shell so as to enclose the absorbent core in the shell. In the preferred embodiment, the facing is a web of through air bonded bicomponent (polyester/polyethylene) fiber. Excellent results have been obtained using such a fabric of 0.7 oz/yd² formed from 3 denier, 1½ bicomponent staple fiber.

A function of peat moss product 21 is to ultimately absorb from receiving layer 22 the liquid which is discharged into pad 10 by the wearer. Thus, peat moss layer 21 must have a liquid absorption capacity sufficiently high to absorb the relatively large amounts of urine which can be expected to be discharged, either by a single large void or by two or more smaller voids, by an incontinent adult over the period of time the urinary device would be worn. Peat moss layer 21 must also function to retain and immobilize said discharged liquid under the pressure encountered as a result of the normal activities of the wearer of the device. When the first portion functions to retain and immobilize liquid, the possibility of discharged liquid flowing back into and through the receiving layer and facing sheet and rewetting the body of the wearer is greatly reduced. Any liquid not absorbed by the receiving layer can be held in the bottom of the cup until absorbed by the peat moss layer. Furthermore, due to the strong liquid extractability properties of peat moss layer 21, discharged liquid is gradually drawn away from facing 21 and receiving layer 22, thus keeping the liquid impact area dry.

The product of the present invention is worn by the wearer in the crotch region, and for simplicity is secured to the underclothing of the wearer. Securement may be effected by the aforementioned adhesive lines or strips on the exterior of the shell, or the product may simply secure itself to the underclothing by means of friction. If the product is to be secured by friction, a material for manufacturing the shell is selected which will provide sufficient friction or a material is coated on the exterior of the shell to provide such friction.

From the foregoing, it will be observed that numerous variations and modifications may be effected without departing from the true spirit and scope of the novel concept of this invention.

The side of receiving layer 22 extend over the side edges of the central portion of absorbent, highly liquid-retentive peat moss layer 21 in assembled pad 10. Referring to FIG. 2, where absorbent unit 13 is shown in its M-folded configuration, it will be seen that the side of receiving layer 22 are disposed between the side walls of shell 12 and the thickened side portions 21a, 21a of peat moss layer 21. It will be understood that said thickened side portions 21a, 21a and the aforementioned M-fold configuration result from the application to absorbent unit 13 of the lateral compressive forces indicated by the directional arrows A,B in FIG. 7. It will be further appreciated that said compressive forces simultaneously act to form liquid receiving channel 23 and provide the configuration of receiving layer 22 shown in FIG. 2.

The so-positioned receiving layer 22 provides a path for liquid to flow between the side walls of shell 12 and the thickened peat moss side portions 21a, 21a.

What is claimed is:

1. In a disposable absorbent product having a wearer-facing side and a bottom side and comprising a liquid-impermeable, substantially flexible shell, open on the wearer-facing side, and containing therein an absorbent core having lengthwise edges; said absorbent product further provided with a liquid permeable facing overlying the wearer-facing side of said absorbent core and being adhered to said shell so as to entrap said absorbent core in said shell; the improvement which comprises:

said absorbent core comprising at least one sheet of tenderized peat moss board, said sheet having lengthwise edges and having, adjacent to each of said lengthwise edges, one or more slits to aid lateral compression folding of said at least one sheet; and adjacent to said at least one sheet and overlying the wearer-facing side thereof, a receiving layer comprising absorbent cellulosic material;

said absorbent core being pleated to form therein a center channel in a lengthwise direction.

2. A product according to claim 1 wherein said shell is a substantially flexible, ethylene-containing polymer foam shell.

3. A product according to claim 2 wherein said shell has a thickness of about 1/64 inch to about ¼ inch.

4. A product according to claim 1 wherein adhesive means are positioned on the bottom surface of said shell for temporarily, but securely, adhering said product to the crotch portion of a nether garment.

5. A product according to claim 1 wherein said receiving layer is capable of absorbing at least about 10 cc of aqueous liquid per second.

6. A product according to claim 1 wherein said receiving layer is a fibrous web comprising between about 50 to 95 weight % wood pulp and about 5 to 50 weight % non-cellulosic synthetic fibers.

7. A product according to claim 6 wherein said receiving layer is a fibrous web comprising about 70–80 weight % wood pulp and about 20–30 weight % non-cellulosic synthetic fibers.

8. A product according to claim 6 wherein said non-cellulosic synthetic fibers comprise bicomponent fibers.

9. A product according to claim 7 wherein said non-cellulosic synthetic fibers comprise bicomponent fibers.

10. A product according to claim 8 wherein said bicomponent fibers comprise a core of polyester and a sheath of polyethylene.

11. A product according to claim 9 wherein said bicomponent fibers comprise a core of polyester and a sheath of polyethylene.

12. A product according to claim 1 wherein said sheet comprises a mixture of peat moss and a cellulosic fibrous material selected from the group consisting of kraft, wood pulp and mechanical wood pulp.

13. A product according to claim 12 wherein said sheet further comprises polyester fibers.

14. A product according to claim 1 wherein said sheet is cut adjacent to each lengthwise edge in a series of lengthwise slits which increase in length from the center of the sheet.

15. A product according to claim 1 wherein said absorbent core comprises at least two sheets of tenderized peat moss board.

16. A product according to claim 1 wherein said liquid-permeable facing is selected from the group consisting of polyester films, polyester fabrics, polyethylene films, polyethylene fabrics, polypropylene films, polypropylene fabrics, bicomponent fiber fabrics, nylon fiber fabrics and rayon fiber fabrics.

17. A product according to claim 16 wherein said liquid-permeable facing comprises a thermally bonded web of polyester/polyethylene bicomponent fiber.

18. A product according to claim 1 wherein said absorbent core is pleated in an M-configuration.

19. In a disposable absorbent product having a wearer-facing side and a bottom side and comprising a liquid-impermeable, substantially flexible shell, open on the wearer-facing side and containing therein an absorbent core having lengthwise edges; said absorbent product further provided with a liquid permeable facing overlying the wearer-facing side of said absorbent core and being adhered to said shell so as to entrap said absorbent core in said shell; the improvement which comprises:

said absorbent core comprising at least one sheet of tenderized peat moss board, said sheet having lengthwise edges and having adjacent to each of said lengthwise edges one or more slits to aid lateral compression folding of said at least one sheet; and adjacent to at least one sheet and overlying the wearer-facing side thereof, a receiving layer comprising a fibrous web comprising about 70 to 80 weight % wood pulp and about 20 to 30 weight % non-cellulosic synthetic fibers; said absorbent core being pleated in an M-configuration to form therein a center channel in a lengthwise direction.

* * * * *